United States Patent
Li et al.

(10) Patent No.: US 10,405,803 B2
(45) Date of Patent: Sep. 10, 2019

(54) METHOD FOR LOW-POWER-CONSUMPTION, ROBUST ESTIMATION OF CARDIOVASCULAR PERIODICITY, CONTOUR ANALYSIS, AND HEART RATE

(71) Applicant: Samsung Electronics Co., LTD, Gyeonggi-Do (KR)

(72) Inventors: Yelei Li, Santa Clara, CA (US); Asif Khalak, Belmont, CA (US)

(73) Assignee: Samsung Electronics Co., Ltd., Gyeonggi-Do (KR)

(*) Notice: Subject to any disclaimer, the term of this patent is extended or adjusted under 35 U.S.C. 154(b) by 597 days.

(21) Appl. No.: 14/928,072

(22) Filed: Oct. 30, 2015

(65) Prior Publication Data

US 2016/0220191 A1  Aug. 4, 2016

Related U.S. Application Data

(60) Provisional application No. 62/113,092, filed on Feb. 6, 2015, provisional application No. 62/112,032, filed on Feb. 4, 2015, provisional application No. 62/110,263, filed on Jan. 30, 2015.

(51) Int. Cl.
| | |
|---|---|
| *A61B 5/00* | (2006.01) |
| *A61B 5/024* | (2006.01) |
| *A61B 5/0402* | (2006.01) |
| *A61B 5/08* | (2006.01) |

(Continued)

(52) U.S. Cl.
CPC ........ *A61B 5/7264* (2013.01); *A61B 5/02416* (2013.01); *A61B 5/0402* (2013.01); *A61B 5/0816* (2013.01); *A61B 5/1455* (2013.01); *A61B 5/7203* (2013.01); *A61B 5/7207* (2013.01); *A61B 5/7221* (2013.01); *A61B 5/7225* (2013.01); *A61B 5/7253* (2013.01);

(Continued)

(58) Field of Classification Search
CPC .......... G01N 33/4833; A61B 5/7264; A61B 5/7225; A61B 5/7203; A61B 5/1455; A61B 5/0816; A61B 5/7221; A61B 5/7207; A61B 5/0402; A61B 5/7253; A61B 5/7278; A61B 5/02416
See application file for complete search history.

(56) References Cited

U.S. PATENT DOCUMENTS

| | | | |
|---|---|---|---|
| 2007/0219453 A1* | 9/2007 | Kremliovsky | A61B 5/0452 600/509 |
| 2009/0105556 A1* | 4/2009 | Fricke | A61B 5/0059 600/301 |

* cited by examiner

*Primary Examiner* — Mark Bockelman (57) ABSTRACT

A computer-implemented method for estimating a cardiovascular feature, such as heart interbeat intervals, using time-delay embedding includes receiving a quasiperiodic observational data stream from a biophysiological sensor, selecting a first delay value, and generating a first vector with a first dimensionality in a multidimensional coordinate space from the observational data stream through time-delay embedding. The method also includes selecting a first plane with a second dimensionality equal to one less than the first dimensionality and which passes through an origin of the coordinate space, identifying a plurality of crossings of the first vector through the first plane in one direction, and correlating a time value corresponding to each of the crossings. The method further includes calculating a plurality of periods between the time values corresponding to consecutive crossings, where the periods represent a stream of interbeat intervals.

16 Claims, 6 Drawing Sheets

(51) Int. Cl.
*A61B 5/1455* (2006.01)
*G01N 33/483* (2006.01)
(52) U.S. Cl.
CPC ....... *A61B 5/7278* (2013.01); *G01N 33/4833* (2013.01)

METHOD FOR LOW-POWER-CONSUMPTION, ROBUST ESTIMATION OF CARDIOVASCULAR PERIODICITY, CONTOUR ANALYSIS, AND HEART RATE

CROSS-REFERENCE TO RELATED APPLICATIONS

This application claims the benefit of U.S. Provisional Application No. 62/110,263, filed Jan. 30, 2015; U.S. Provisional Application No. 62/112,032, filed Feb. 4, 2015; and U.S. Provisional Application No. 62/113,092, filed Feb. 6, 2015, which are incorporated by reference herein.

TECHNICAL FIELD

This description relates generally to signal processing, and more particularly to a method for low-power-consumption, robust estimation of cardiovascular periodicity, contour analysis, and heart rate.

BACKGROUND

Signal processing generally encompasses collecting, organizing, transforming and summarizing raw input data to produce meaningful or useful information, or output data. Signal processing typically manipulates large amounts of numeric data, and may include processes such as sorting, formatting, aggregation, classification, validation, and reporting the data.

A delay embedding theorem specifies the conditions under which a chaotic dynamical system may be reconstructed from a sequence of observations of the state of a dynamical system. In general, the reconstruction should preserve the properties of the dynamical system that do not change under smooth coordinate changes, but not necessarily the geometric shape of structures in phase space. For example, Takens' theorem (1981) provides a delay embedding theorem that provides the conditions under which the underlying dynamics of a physical system may be reconstructed from an observed time series, given a sufficient number of observations at equally spaced times.

Cardiovascular periodicity generally refers to the nearly regular, recurrent blood pressure and volume pulses induced by the heart. The time length of each period between consecutive individual heart beats is commonly referred to as the interbeat interval (IBI, or RR interval). The heart rate is the inverse of the cardiovascular periodicity.

During normal heart functioning, there is some variation in the continuous time series of IBI values. This natural variation is known as heart rate variability (HRV). Relatively noisy or low-amplitude sensor signals may add measurement error that further detracts from the nearly periodic nature of the observed heart beat signal. Thus, the observed heart beat sensor signal typically represents a quasiperiodic function. That is, the signal is similar to a periodic function, but displays irregular periodicity and does not meet the strict definition of a periodic function that recurs at regular intervals. Quasiperiodic behavior includes a pattern of recurrence with a component of unpredictability that does not lend itself to precise measurement.

The time intervals between consecutive heart beats are customarily measured in an electrocardiogram (ECG or EKG) from the initiation of each of two consecutive QRS complexes, corresponding to the contraction of the heart ventricles, each of which typically includes three component waveforms (the Q-wave, R-wave and S-wave). However, the initiation of the QRS complex may be difficult to locate in relatively noisy or low-amplitude sensor signals, which may lead to measurement error. Thus, IBI is sometimes measured between R-wave peaks in consecutive heart beats to reduce measurement error.

IBI may also be determined from a peripheral pulse measurement, such as a digital volume pulse measurement, such as a photoplethysmogram (PPG), an optically obtained plethysmogram, or volumetric measurement of an organ. PPG sensors have been used to monitor respiration and heart rates, blood oxygen saturation, hypovolemia, and other circulatory conditions.

The pulse oximeter, a known type of PPG sensor, illuminates the skin with one or more colors of light and measures changes in light absorption at each wavelength. The PPG sensor illuminates the skin, for example, using an optical emitter, such as a light-emitting diode (LED), and measures either the amount of light transmitted through a relatively thin body segment, such as a finger or earlobe, or the amount of light reflected from the skin, for example, using a photodetector, such as a photodiode.

Conventional PPGs typically monitor the perfusion of blood to the dermis and subcutaneous tissue of the skin, which may be used to detect, for example, the change in volume corresponding to the pressure pulses of consecutive cardiac cycles of the heart. If the PPG is attached without compressing the skin, a secondary pressure peak may also be seen from the venous plexus. A microcontroller typically processes and calculates the peaks in the waveform signal to count heart beats per minute (bpm).

Lorenz, or Poincaré, plots of RR intervals, in which each data point represents a pair of successive beats, with the current RR interval plotted against the previous RR interval, have been used as a geometric or graphical non-linear method to evaluate HRV. These plots permit visualization of higher-dimensional phase spaces in subspaces with relatively low dimensionality, for example, two- or three-dimensional subspaces. In some analyses, mathematically-defined geometric shapes—such as elliptic, linear, or triangular shapes—have been fitted to the overall data pattern. In other analyses, the dispersion of points along or orthogonal to the axis of the identity line, or line of equality, has been evaluated.

SUMMARY

According to one embodiment, a device includes a memory that stores machine instructions and a processor coupled to the memory that executes the machine instructions to generate a first coordinate corresponding to a first time along a first dimension from a data stream, generate a second coordinate corresponding to a second time along a second dimension, wherein the second time varies from the first time by a time delay value, and wherein the second dimension is of a higher dimension than the first dimension, generate a first vector trajectory based on the first coordinate and the second coordinate, and determine a cardiovascular feature based on determining a plurality of primary crossing points of the vector trajectory intersecting a desired decision line.

According to another embodiment, a method includes generating a first coordinate corresponding to a first time along a first dimension from a data stream, generating a second coordinate corresponding to a second time along a second dimension, wherein the second time varies from the first time by a time delay value, and wherein the second dimension is of a higher dimension than the first dimension, generating a first vector trajectory based on the first coordinate and the second coordinate, and determining a cardiovascular feature based on determining a plurality of primary crossing points of the vector trajectory intersecting a desired decision line.

According to another embodiment, a computer program product includes a non-transitory, computer-readable storage medium encoded with instructions adapted to be executed by a processor to implement generating a first coordinate corresponding to a first time along a first dimension from a data stream, generating a second coordinate corresponding to a second time along a second dimension, wherein the second time varies from the first time by a time delay value, and wherein the second dimension is of a higher dimension than the first dimension, generating a first vector trajectory based on the first coordinate and the second coordinate, and determining a cardiovascular feature based on determining a plurality of primary crossing points of the vector trajectory intersecting a desired decision line.

The details of one or more embodiments of the present disclosure are set forth in the accompanying drawings and the description below. Other features, objects, and advantages of the present disclosure will be apparent from the description and drawings, and from the claims.

DETAILED DESCRIPTION

According to one embodiment, the present system processes a stream of biophysiological sensor data over time and outputs a stream of biophysiological feature data, for example, interbeat intervals or instantaneous heart rates. The process implements time-delay embedding, which involves constructing multiple coordinates associated with a series of time delays in the system.

The present system and method provides a low-power-consumption method of determining cardiovascular periodicity, contour analysis, and heart rate in a cardiovascular measurement environment where biophysiological sensors and associated microcontrollers are powered by relatively small batteries, according to one embodiment. The present system and method further determines cardiovascular periodicity, contour analysis, and heart rate that is robust with regard to signal noise and artifacts.

Figure 1:
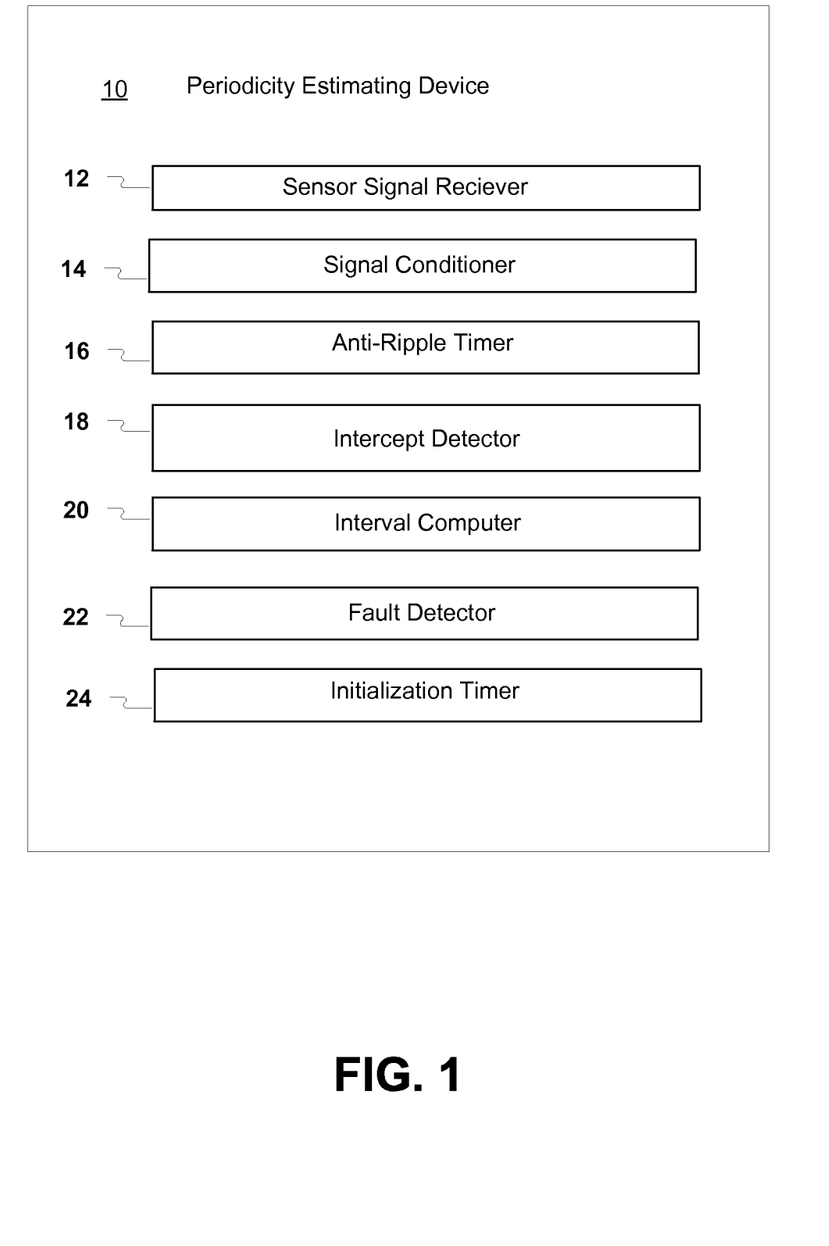
FIG. 1 illustrates a block diagram depicting an exemplary periodicity estimating device in accordance with an embodiment.

FIG. 1 illustrates a block diagram depicting an exemplary periodicity estimating device in accordance with an embodiment. An exemplary periodicity estimating device 10 employs a time-delay embedding process in order to estimate cardiovascular periodicity, contour analysis and heart rate. The periodicity estimating device 10 includes a sensor signal receiver 12, a signal conditioner 14, an anti-ripple timer 16, an intercept detector 18, an interval computer 20, a fault detector 22, and an initialization timer 24.

The sensor signal receiver 12 receives biophysiological sensor data as input, for example, a photoplethysmogram (PPG) sensor signal. In various embodiments, biophysiological sensor data that may be analyzed by the periodicity estimating device 10 include, but are not limited to, optical sensor data (e.g., PPG), electrical potential sensor data (e.g., an electrocardiogram (ECG or EKG)), electrical impedance sensor data (e.g., Bio Z® impedance cardiography (ICG)).

The signal conditioner 14 plots the input signal with respect to a delayed signal, for example, a fixed delay. The anti-ripple timer 16 sets the signal to zero during an anti-ripple period. The intercept detector 18 removes relatively high-frequency components of the sensor signal, implements time-delay embedding with respect to the signal derivative, and detects intercepts, or zero crossings.

For example, for a particular measurement time series function, s(t), the coordinates:

$$\{s(t), s(t-500)\}$$

may be used to reconstruct the corresponding phase trajectory. The coordinates are plotted with respect to the x-axis and the y-axis, respectively, in two-dimensional coordinate space. In this example, the coordinates represent a current observational sample at time t along the x-axis, and the sample observed 500 milliseconds (ms) earlier than time t along the y-axis. In other embodiments, the time delay value may vary. For example, the time delay could be 100 ms, 200 ms, 300 ms, 900 ms, 1200 ms, or any other useful value in various embodiments.

In an alternative embodiment, the phase trajectory corresponding to the time series function may be reconstructed in coordinate spaces of higher dimensionality using multiples of the time delay value as the function variable along each axis. For example, for the above measurement time series function, s(t), the coordinates:

$$\{s(t), s(t-500), s(t-1000)\}$$

may be used to create a three-dimensional vector in three-dimensional coordinate space. In this example, the coordinates represent a current observational sample at time t along the x-axis, the sample observed 500 ms earlier than time t along the y-axis, and the sample observed 1000 ms earlier than time t along the z-axis. In various embodiments, the time delay value may vary. For example, the time delay is 100 ms, 200 ms, 300 ms, 900 ms, 1200 ms, or any value in various embodiments.

The interval computer 20 calculates the period between zero crossings, for example, to determine the interbeat interval (IBI) of a subject heart. The fault detector 22 sets the output to a default value when a fault condition is detected, for example, excessive sensor motion or outlier data. The initialization timer 24 temporarily sets the output signal to a default value when the periodicity estimating process is initiated in order to allow the process output to reach a steady state.

Figure 2:
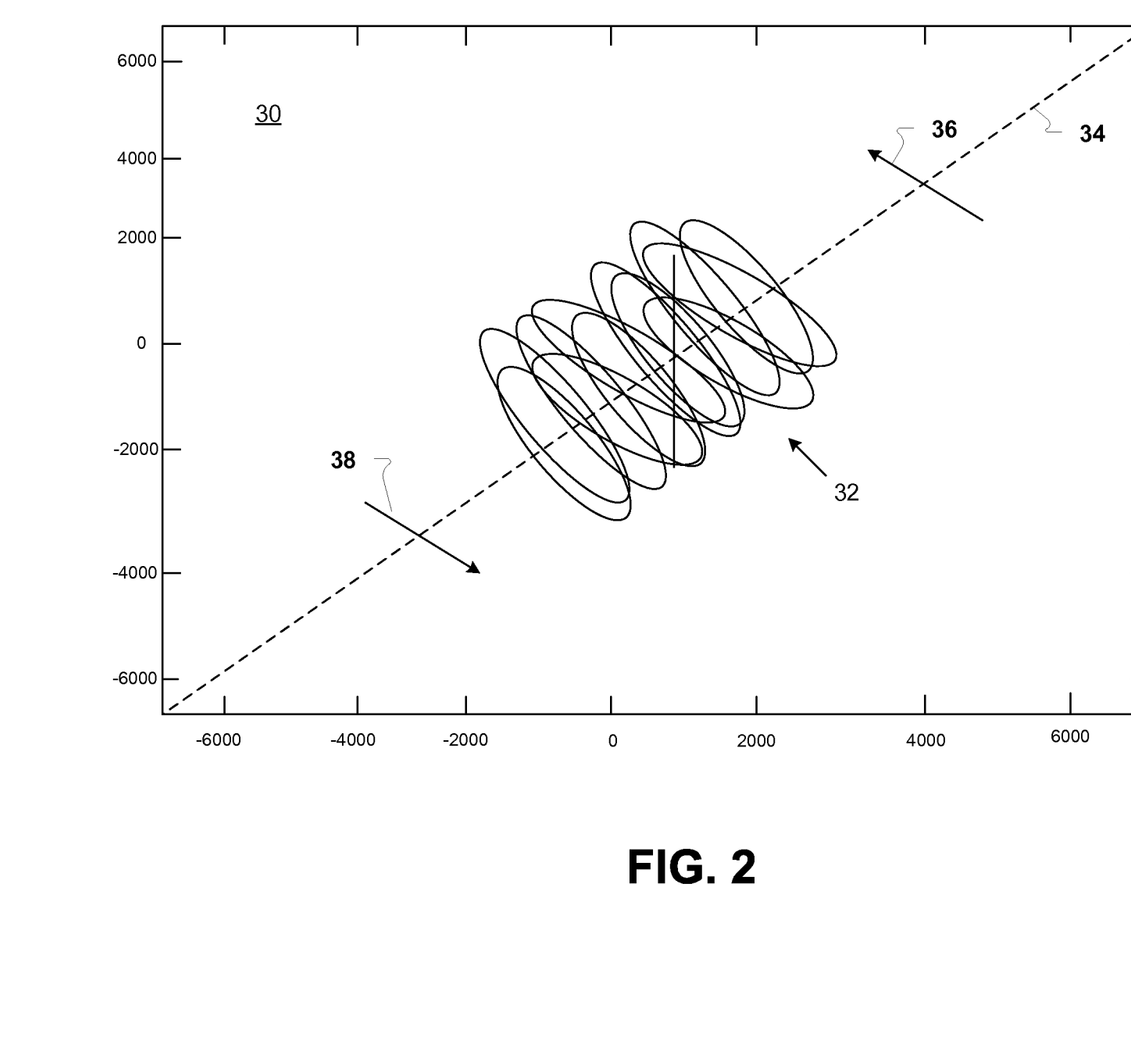
FIG. 2 illustrates a graphical plot of an exemplary two-dimensional reconstruction of the phase trajectory corresponding to a time series of observational data in accordance with an embodiment.

FIG. 2 illustrates a graphical plot of an exemplary two-dimensional reconstruction of the phase trajectory corresponding to a time series of observational data in accordance with an embodiment. An exemplary trace 30 illustrates several cycles of a two-dimensional reconstruction. The trajectory of the vector 32 with respect to the x-axis and the y-axis is evaluated for crossings at the line 34, or ray, passing through the coordinate space origin (0,0) at a 45-degree angle. The vector 32 crosses a desired line 34 at several points along the line 34. The arrows 36 and 38 indicate the direction of the orbit. Each time the vector 32 crosses the line 34 in a particular direction (for example, from left to right in FIG. 2) indicates the start of a cycle, or period. For the two-dimensional reconstruction, the desired line is of one dimension.

In an alternative embodiment using more than one time delay, for example, to create a trace that illustrates several cycles of a three-dimensional reconstruction in a three-dimensional coordinate space, crossings through a plane of two dimensions are evaluated. In another embodiment, a trace that illustrates several cycles of a four-dimensional reconstruction is created in a four-dimensional coordinate space, and crossings through a shape of three dimensions are evaluated.

In an alternative embodiment, multiple time delay values are used to create additional complementary results, such as a distribution of periods based on different time delays. For example, separate reconstructions of a particular dimensionality may be created using time delays of 150 ms, 300 ms and 450 ms. In this case, further statistical calculations or inferences may be performed based on the resulting distribution (three sets) of periods.

In another alternative embodiment, multiple selections of the cycle-cut plane are used to create additional complementary results, such as a distribution of periods based on different cycle-cut planes. For example, cycle-cut planes at 30 degrees, 45 degrees and 60 degrees may be used in a reconstruction of a particular dimensionality. Further statistical calculations or inferences may be performed based on the resulting distribution of periods.

In yet another alternative embodiment, multiple time delay values as well as multiple selections of the cycle-cut plane are used to create additional complementary results, such as a distribution of periods based on different time delay values with different cycle-cut planes. For example, separate reconstructions of a particular dimensionality may be created using time delays of 150 ms, 300 ms and 450 ms, and each may be evaluated using three different selections of cycle-cut planes at 30 degrees, 45 degrees and 60 degrees. Further statistical calculations or inferences may be performed based on the resulting distribution of periods.

Figure 3A:
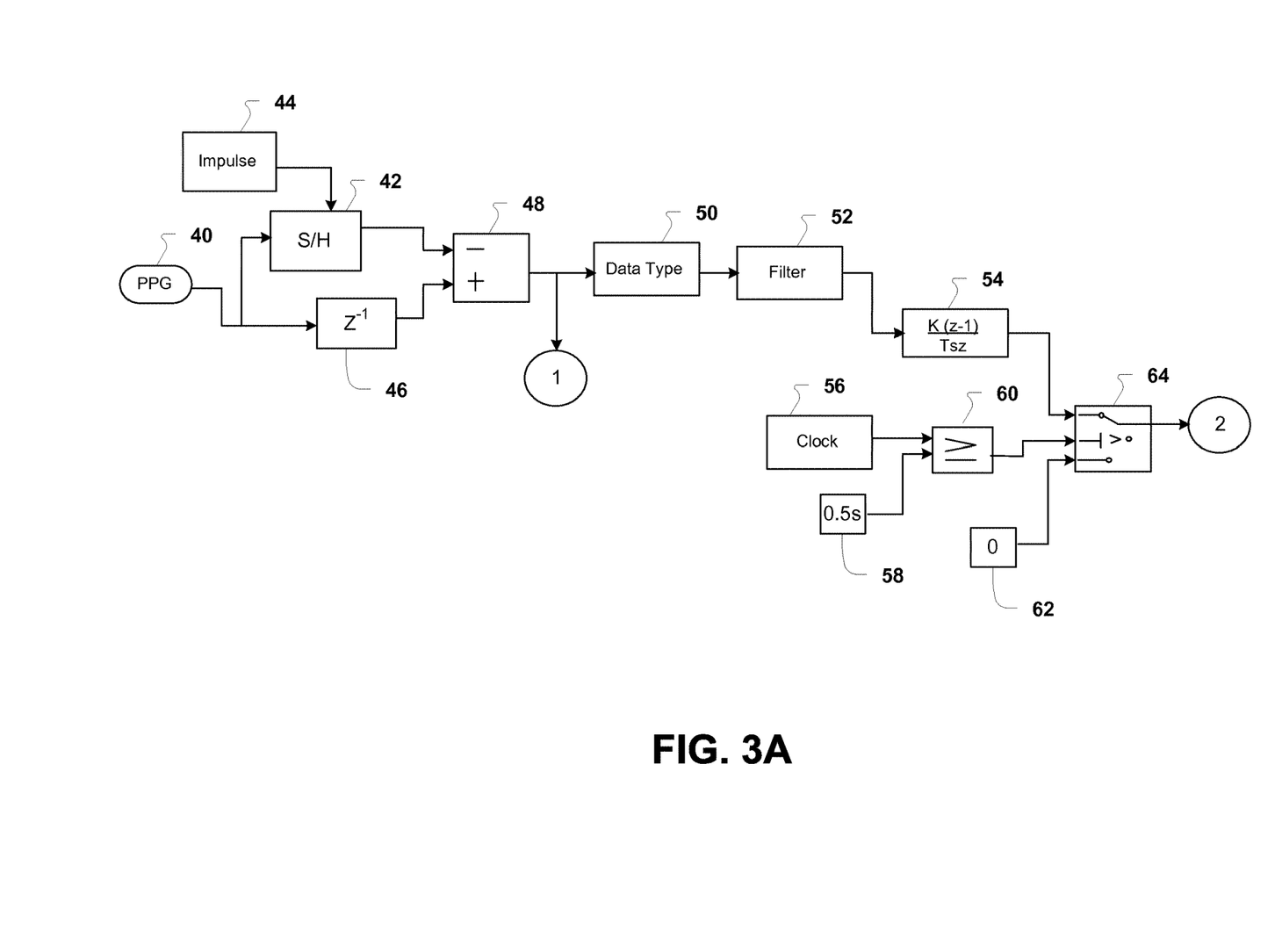
FIG. 3A illustrates a logic diagram representing an exemplary method of estimating cardiovascular periodicity in accordance with an embodiment.

FIG. 3A illustrates a logic diagram representing an exemplary method of estimating cardiovascular periodicity in accordance with an embodiment. A method for using time-delay embedding to estimate cardiovascular periodicity, contour analysis, and heart rate is performed by a periodicity estimating device, according to one embodiment. A PPG sensor 40 detects an input signal, for example a cardiovascular periodic signal. At 42, the input signal is sampled and held and combined with a discrete impulse signal 44. At 46, a fixed integer delay (e.g., "$Z^{-1}$") is applied to the input signal to derive a delayed signal. At 48, the output signal of 42 is subtracted from the delayed signal. The output signal of 48 is forwarded to a buffer 100 of FIG. 3C for further processing, as indicated by the reference numeral "1".

At 50, the digital data type of the output signal of 48 is converted, for example, to a double-precision floating-point number. At 52, the relatively high-frequency components of the output signal of 50 are removed using a low-pass filter. At 54, the discrete derivative of the output signal of 52 with respect to time is calculated.

A digital clock 56 is reset to zero at the initiation of an anti-ripple period. At 60, an anti-ripple hold-off time 58, for example, 0.5 seconds, is compared to the digital clock 56 using a relational operator (e.g., "≥"). At 64, during an anti-ripple period, a default output (e.g., zero) 62 is used, otherwise, the discrete derivative from 54 is used. The output signal of 64 is forwarded to 70, 76, and 78 of FIG. 3B for further processing, as indicated by the reference numeral "2".

Figure 3B:
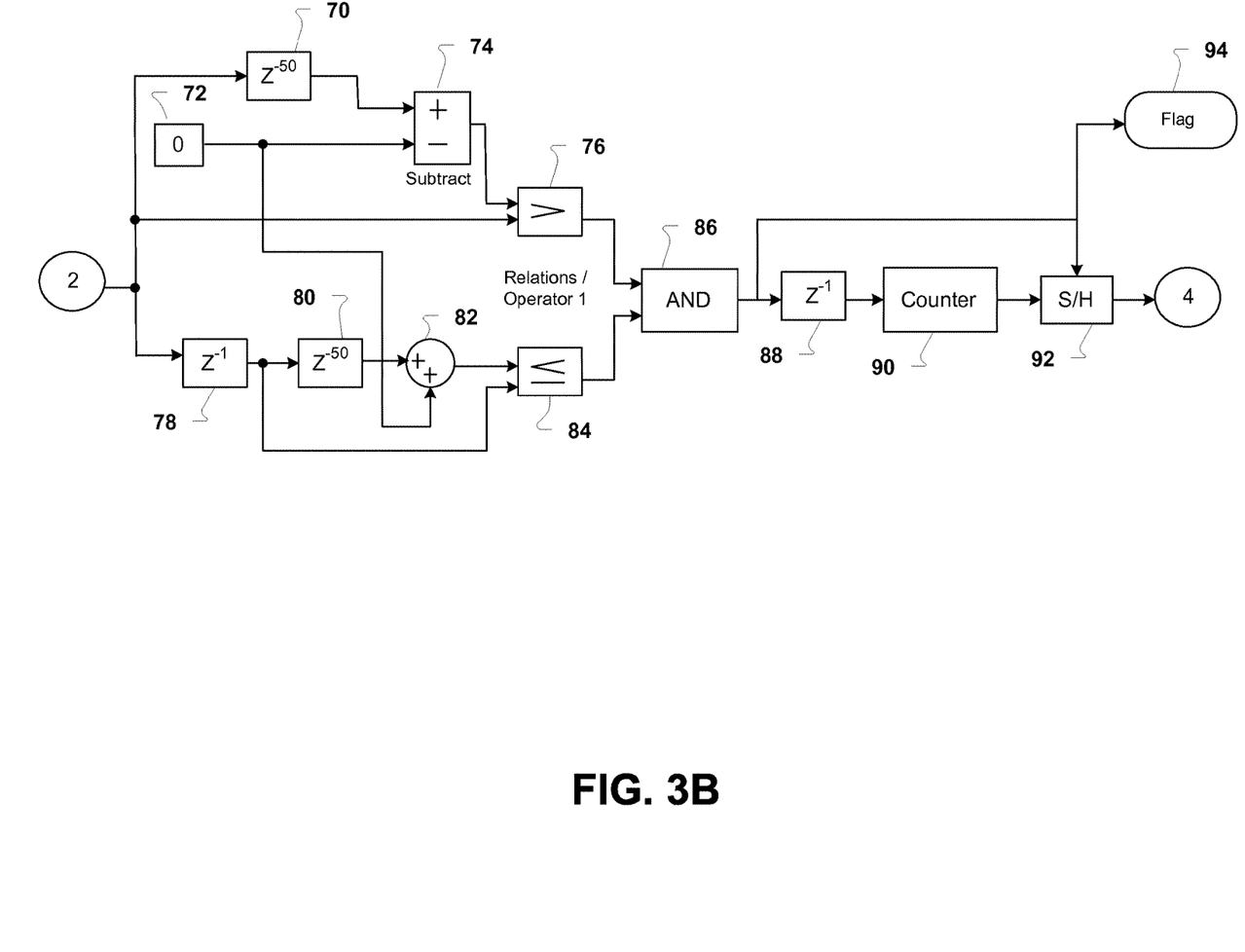
FIG. 3B illustrates another logic diagram representing an exemplary method of estimating cardiovascular periodicity in accordance with an embodiment.

FIG. 3B illustrates another logic diagram representing an exemplary method of estimating cardiovascular periodicity in accordance with an embodiment. At 70, a current-point time delay (e.g., 50 seconds) is applied to the output signal of 64 of FIG. 3A. It is appreciated that the current-point time delay may be any value without deviating from the scope of the present disclosure. At 74, a robustness offset constant (e.g., zero) 72 is subtracted from the output signal of 70. At 76, the difference output signal of 74 is compared to the output signal of 64 of FIG. 3A using a relational operator (e.g., ">").

At 78, a one-point lag is applied to the output signal of 64. At 80, a previous-point time delay (e.g., 50 seconds) is applied to the output signal of 78. It is appreciated that the previous-point time delay may be any value without deviating from the scope of the present disclosure. At 82, the output signal of 80 is added to the robustness offset constant 72. At 84, the summation output signal of 82 is compared to the output signal of 78 using a relational operator (e.g., "≤"). At 86, time-delay embedding zero crossing points are detected based on the output signals of 76 and 84 being true, or positive. If a zero-crossing point is detected, a zero-crossing flag is forwarded as an input to 92 and provided as an IBI flag output at 94.

At 88, a one-point lag is applied to the detected zero-crossing point output of 86 to compute the interbeat interval. At 90, the interbeat interval is calculated, for example, using a counter that is reset each time a zero-crossing is detected. At 92, a current counter value output of 90 is sampled and held and the output signal of 92 is forwarded to 122 of FIG. 3C for further processing, as indicated by the reference numeral "4".

Figure 3C:
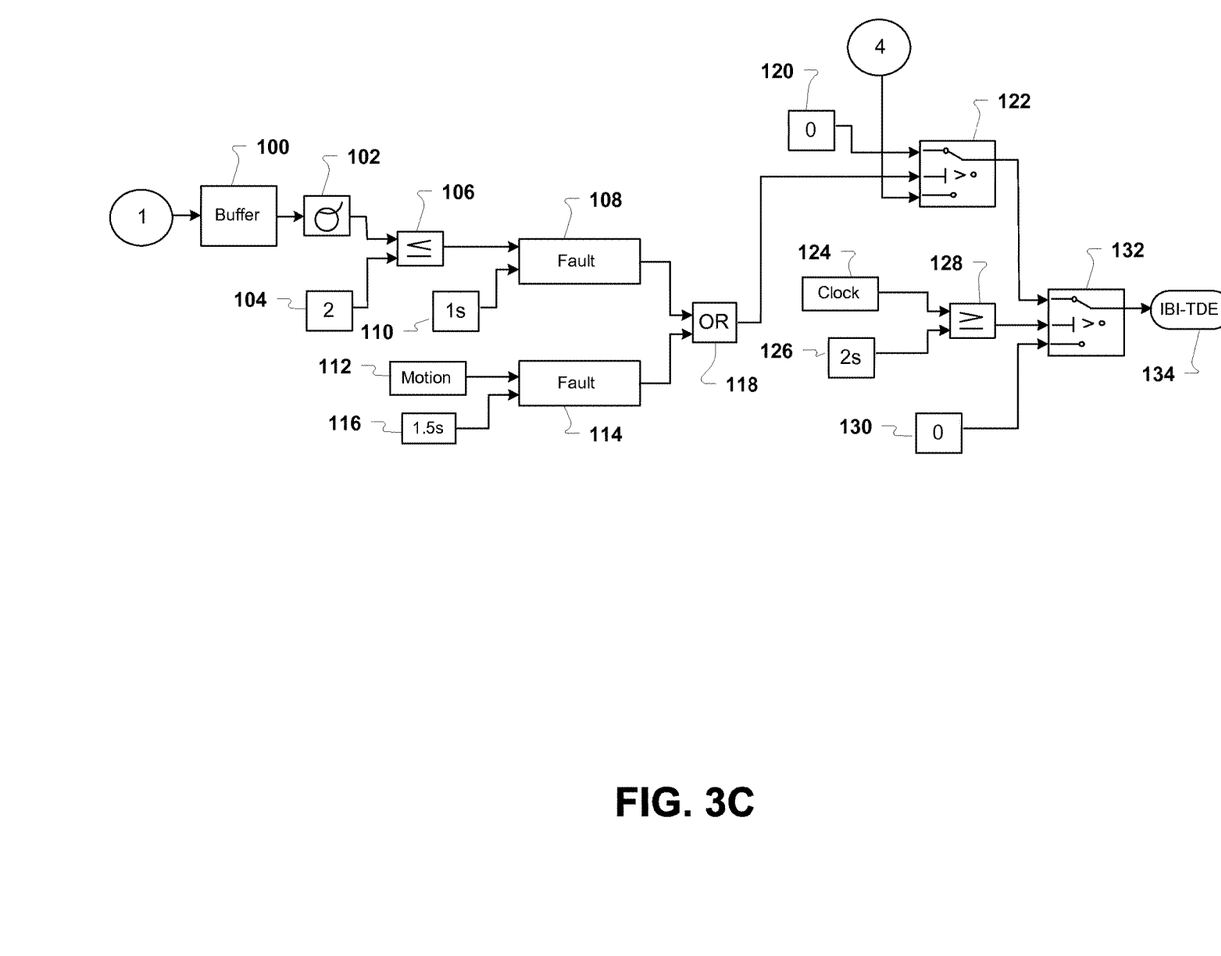
FIG. 3C illustrates another logic diagram representing an exemplary method of estimating cardiovascular periodicity in accordance with an embodiment.

FIG. 3C illustrates another logic diagram representing an exemplary method of estimating cardiovascular periodicity in accordance with an embodiment. The output signal of 48 of FIG. 3A is buffered at 100. At 102, the standard deviation of the buffered output signal of 100 is computed. At 106, the output signal of 102 is compared to a constant 104, using a relational operator (e.g., "≤"). At 108, if the comparison output of 106 is true, a fault is detected (e.g., "flat spot") and a hysteresis fault flag 110 is applied during a fault hysteresis time.

At 114, if a sensor motion detected flag 112 is received, a fault is detected (e.g., "motion detected") and a hysteresis fault flag 116 is applied during a fault hysteresis time. If a fault is detected from the output of 108 or 114 at 118, a masked value 120 is used at 122, otherwise, the output signal value of 92 of FIG. 3B is used.

A digital clock 124 is reset to zero at a process initialization. At 128, an initialization time 126, for example, two seconds is compared to the digital clock 124 using a relational operator (e.g., "≥") to derive an initialization period. At 132, during an initialization period, a default output (e.g., zero) 130 is used, otherwise, the output value of 122 is used. The resulting interval (e.g., IBI) is provided as an output at 134.

The following pseudocode implements an embodiment of the method described in this disclosure for estimating cardiovascular periodicity, contour analysis and heart rate:

Start with a quasiperiodic biophysiological sensor signal, s(t), such as ECG, PPG, Bio Z®, etc.
Select a delay value, deltaT
Create Embedding: Generate an n-vector, x(t) where x(t)={s(t−n*deltaT), s(t−(n−1)*deltaT), . . . , s(t)}. (This entails a minimum startup time of n*deltaT.)
Based on the n-dimensional coordinate space corresponding to the defined coordinates, choose a (n−1)-plane that passes through the signal trajectory. (This plane should have a specified orientation and is called the "cycle-cut plane.")
Look for crossings of x(t) through the cycle-cut plane, and annotate each crossing with the direction that it crosses. For each value oft, generate a flag that indicates whether the plane has been crossed in that sample.
Record the times associated with crossings in a certain direction: $(T_1, T_2, T_3, \ldots)$
Calculate the ibi (inter-beat interval) periods associated with this as $(T_2-T_1, T_3-T_2, \ldots)$
Output this stream of ibi's Referring again to FIGS. 3A, 3B and 3C, the illustrated process flow represents the case of n=2 with a single selection of the cycle-cut plane as the 45-degree plane crossing through the origin. In alternative embodiments, the pseudocode may be modified to generate a distribution of IBI periods based on different values of the time delay (deltaT) and different selections of the cycle-cutting plane.

Because the disclosed approach does not require complex calculations, and requires only a few operations per sample, the process may be performed using relatively low power consumption. This may be advantageous in some environments, for example, in an embedded microcontroller powered by a small battery. In addition, the process is relatively robust, especially in environments having relatively low signal-to-noise ratio (SNR), or with intermittent noise, because excursions that are not large enough to cause line or plane crossings are ignored in further calculations.

Figure 4:
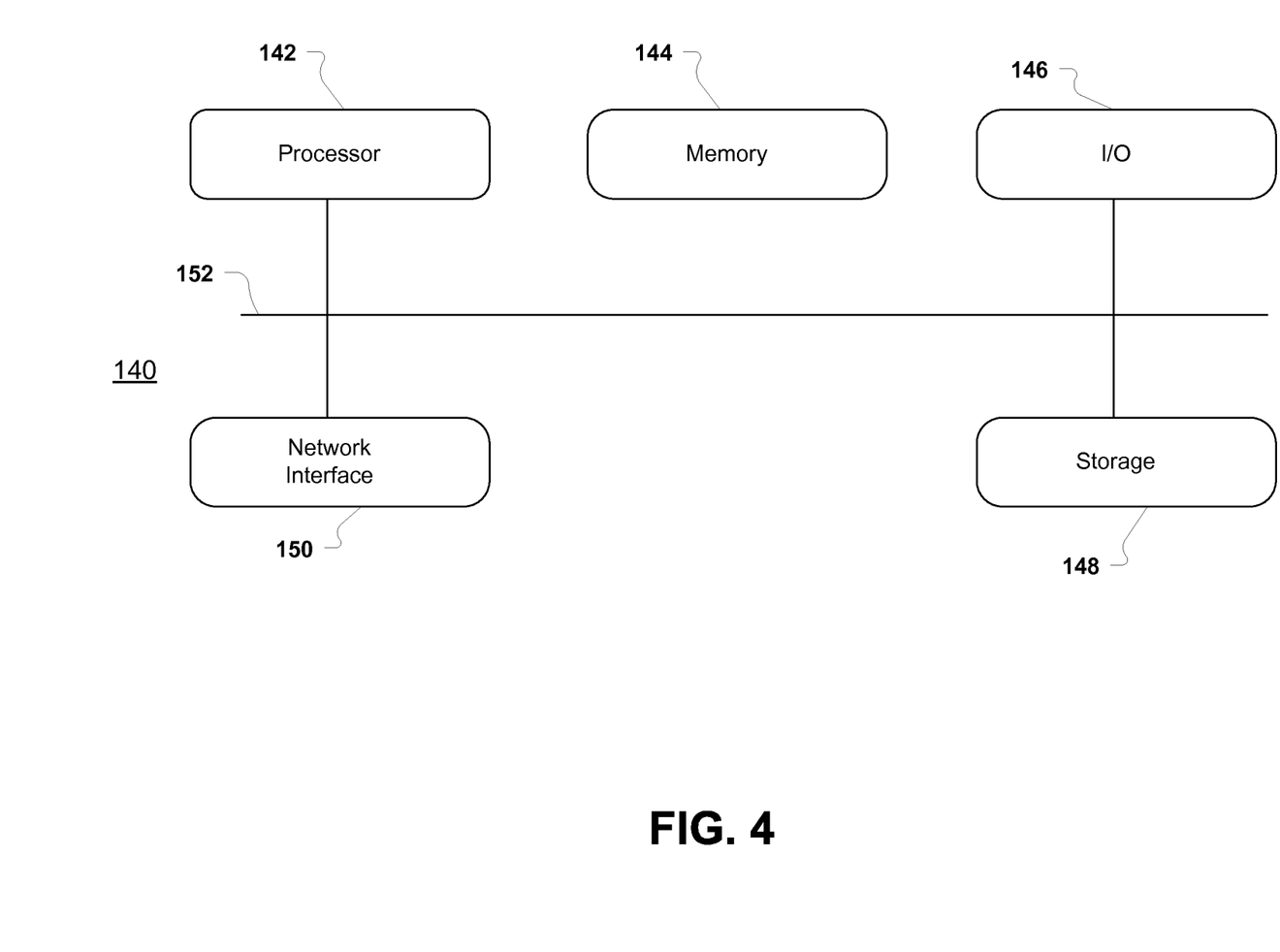
FIG. 4 is a schematic view depicting an exemplary computing system that implements a periodicity estimating device in accordance with an embodiment.

As illustrated in FIG. 4, an exemplary computing device 140 may implement a periodicity estimating device including a processor 142, a memory 144, an input/output device (I/O) 146, storage 148 and a network interface 150. The various components of the computing device 140 are coupled by a local data link 152, which in various embodiments incorporates, for example, an address bus, a data bus, a serial bus, a parallel bus, or any combination of these.

The computing device 140 may be used, for example, to implement a method of using time-delay embedding to estimate cardiovascular periodicity, contour analysis, and heart rate. Programming code, such as source code, object code or executable code, stored on a computer-readable medium, such as the storage 148 or a peripheral storage component coupled to the computing device 140, may be loaded into the memory 144 and executed by the processor 142 in order to perform the functions of the method of using time-delay embedding to estimate cardiovascular periodicity, contour analysis and heart rate of FIG. 1.

Aspects of this disclosure are described herein with reference to flowchart illustrations or block diagrams, in which each block or any combination of blocks may be implemented by computer program instructions. The instructions may be provided to a processor of a general purpose computer, special purpose computer, or other programmable data processing apparatus to effectuate a machine or article of manufacture, and when executed by the processor the instructions create means for implementing the functions, acts or events specified in each block or combination of blocks in the diagrams.

In this regard, each block in the flowchart or block diagrams may correspond to a module, segment, or portion of code that including one or more executable instructions for implementing the specified logical function(s). It should also be noted that, in some alternative implementations, the functionality associated with any block may occur out of the order noted in the figures. For example, two blocks shown in succession may, in fact, be executed substantially concurrently, or blocks may sometimes be executed in reverse order.

A person of ordinary skill in the art will appreciate that aspects of this disclosure may be embodied as a device, system, method or computer program product. Accordingly, aspects of this disclosure, generally referred to herein as circuits, modules, components or systems, may be embodied in hardware, in software (including firmware, resident software, micro-code, etc.), or in any combination of software and hardware, including computer program products embodied in a computer-readable medium having computer-readable program code embodied thereon.

It will be understood that various modifications may be made. For example, useful results still could be achieved if steps of the disclosed techniques were performed in a different order, and/or if components in the disclosed systems were combined in a different manner and/or replaced or supplemented by other components. Accordingly, other implementations are within the scope of the following claims.

What is claimed is:

1. A device operable for estimating cardiovascular periodicity, the device comprising:
a memory having machine instructions stored therein;
a processor coupled to the memory;
a biophysiological sensor coupled to the processor and operable for detecting a cardiovascular periodic signal; and
an input/output device coupled to the processor;
wherein the processor executes the machine instructions to determine the cardiovascular periodicity, wherein the processor executes the machine instructions to:
generate, from a data stream comprising the cardiovascular periodic signal, a first coordinate corresponding to a first time along a first dimension of coordinate space comprising N dimensions, where N is an integer,
generate, from the data stream, a second coordinate corresponding to a second time along a second dimension of the coordinate space, wherein the second time varies from the first time by a time delay value,
generate a first vector trajectory based on the first coordinate and the second coordinate,
determine the cardiovascular periodicity based on determining a plurality of crossing points of the vector trajectory intersecting a geometric element in the coordinate space, the geometric element having N−1 dimensions; and
output a biophysiological feature based on the cardiovascular periodicity to the input/output device.

2. The device of claim 1, wherein the biophysiological sensor comprises a photoplethysmogram (PPG) sensor.

3. The device of claim 1, wherein N is set equal to two and the geometric element is a line, wherein the processor further executes the machine instructions to:

determine a plurality of primary crossing points of the vector trajectory intersecting the line in a direction, wherein the line passes through an origin of the coordinate space;

correlate a plurality of primary time values with the primary crossing points, each primary time value corresponding to a respective primary crossing point; and calculate a plurality of primary periods between the primary time values corresponding to consecutive primary crossing points, wherein the plurality of primary periods represents a primary stream of interbeat intervals comprising the biophysiological feature.

4. The device of claim 3, wherein N is set equal to three and the geometric element is a plane, wherein the processor further executes the machine instructions to:

generate, from the data stream, a third coordinate corresponding to a third time along a third dimension of the coordinate space, wherein the third time varies from the second time by the time delay value;

generate a second vector trajectory based on the first coordinate, the second coordinate, and the third coordinate;

determine a plurality of secondary crossing points of the second vector trajectory through the plane in a direction, correlate a plurality of secondary time values with the plurality of secondary crossing points, each secondary time value corresponding to a respective secondary crossing point, and calculate a plurality of secondary periods between the secondary time values corresponding to consecutive secondary crossings, wherein the plurality of secondary periods represents a secondary stream of interbeat intervals further comprising the biophysiological feature.

5. The device of claim 3, wherein the processor further executes the machine instructions to calculate a reciprocal of each of the plurality of primary periods, wherein the reciprocal represents a heart rate further comprising the biophysiological feature.

6. The device of claim 3, wherein the processor further executes the machine instructions to:

generate a third coordinate corresponding to a third time along the second dimension, wherein the third time varies from the first time by a second time delay value, generate a second vector trajectory based on the first coordinate and the third coordinate;

determine a plurality of secondary crossing points of the second vector trajectory intersecting the geometric element;

correlate a plurality of secondary time values with the secondary crossing points, each secondary time value corresponding to a respective secondary crossing point;

calculate a plurality of secondary periods between the secondary time values corresponding to consecutive secondary crossing points, the plurality of secondary periods representing a secondary stream of interbeat intervals further comprising the biophysiological feature; and perform a statistical inference based on a distribution of the primary stream of interbeat intervals and the secondary stream of interbeat intervals.

7. The device of claim 6, wherein the processor further executes the machine instructions to calculate a reciprocal of each of the plurality of secondary periods, wherein the reciprocal represents a heart rate comprising the biophysiological feature.

8. The device of claim 1, wherein the processor further executes the machine instructions to provide a default output value based on a fault having been detected.

9. A method to determine cardiovascular periodicity, the method comprising:

detecting a cardiovascular periodic signal with a biophysiological sensor;

generating, from a data stream comprising the cardiovascular periodic signal and with a processor, a first coordinate corresponding to a first time along a first dimension of coordinate space comprising N dimensions, wherein N is an integer;

generating, from the data stream and with the processor, a second coordinate corresponding to a second time along a second dimension of the coordinate space, wherein the second time varies from the first time by a time delay value;

generating, with the processor, a first vector trajectory based on the first coordinate and the second coordinate;

determining, with the processor, the cardiovascular periodicity based on determining a plurality of crossing points of the vector trajectory intersecting a geometric element in the coordinate space, the geometric element having N−1 dimensions; and outputting, to an input/output device, a biophysiological feature based on the cardiovascular periodicity.

10. The method of claim 9, wherein the biophysiological sensor comprises a photoplethysmogram (PPG) sensor.

11. The method of claim 9, wherein N is set equal to two and the geometric element is a line, the method further comprising:

determining a plurality of primary crossing points of the vector trajectory intersecting the line in a direction, wherein the line passes through an origin of the coordinate space;

correlating a plurality of primary time values with the primary crossing points, each primary time value corresponding to a respective primary crossing point; and calculating a plurality of primary periods between the primary time values corresponding to consecutive primary crossing points, wherein the plurality of primary periods represents a primary stream of interbeat intervals comprising the biophysiological feature.

12. The method of claim 11, wherein N is set equal to three and the geometric element is a plane, the method further comprising:

generating, from the data stream, a third coordinate corresponding to a third time along a third dimension of the coordinate space, wherein the third time varies from the second time by the time delay value;

generating a second vector trajectory based on the first coordinate, the second coordinate, and the third coordinate;

determining a plurality of secondary crossing points of the second vector trajectory through the plane in a direction;

correlating a plurality of secondary time values with the plurality of secondary crossing points, each secondary time value corresponding to a respective secondary crossing point; and calculating a plurality of secondary periods between the secondary time values corresponding to consecutive secondary crossings, wherein the plurality of secondary periods represents a secondary stream of interbeat intervals further comprising the biophysiological feature.

13. The method of claim 11, further comprising calculating a reciprocal of each of the plurality of primary periods, wherein the reciprocal represents a heart rate further comprising the biophysiological feature.

14. The method of claim 11, further comprising:
generating a third coordinate corresponding to a third time along the second dimension, wherein the third time varies from the first time by a second time delay value,
generating a second vector trajectory based on the first coordinate and the third coordinate;
determining a plurality of secondary crossing points of the second vector trajectory intersecting the geometric element;
correlating a plurality of secondary time values with the secondary crossing points, each secondary time value corresponding to a respective secondary crossing point;
calculating a plurality of secondary periods between the secondary time values corresponding to consecutive secondary crossing points, the plurality of secondary periods representing a secondary stream of interbeat intervals further comprising the biophysiological feature; and
performing a statistical inference based on a distribution of the primary stream of interbeat intervals and the secondary stream of interbeat intervals.

15. The method of claim 14, further comprising calculating a reciprocal of each of the plurality of secondary periods, wherein the reciprocal represents a heart rate further comprising the biophysiological feature.

16. The method of claim 9, further comprising providing a default output value based on a fault having been detected.

* * * * *